(12) United States Patent
DeVitis

(10) Patent No.: US 7,757,331 B2
(45) Date of Patent: Jul. 20, 2010

(54) ELECTRIC TOOTHBRUSH ATTACHMENT FOR BACKSIDE CLEANING

(76) Inventor: Louis DeVitis, 743 Perrineville Rd., Perrineville, NJ (US) 08535-1041

( * ) Notice: Subject to any disclaimer, the term of this patent is extended or adjusted under 35 U.S.C. 154(b) by 986 days.

(21) Appl. No.: 11/374,232

(22) Filed: Mar. 13, 2006

(65) Prior Publication Data

US 2007/0209127 A1    Sep. 13, 2007

(51) Int. Cl.
  *A61C 17/26* (2006.01)
  *A46B 13/02* (2006.01)
(52) U.S. Cl. ............... 15/28; 15/22.1; 15/22.2; 15/22.4
(58) Field of Classification Search ............ 15/22.1, 15/22.2, 22.4, 28, 29, 23
  See application file for complete search history.

(56) References Cited

U.S. PATENT DOCUMENTS

| | | | | |
|---|---|---|---|---|
| 1,320,616 A | * | 11/1919 | Hampe | 15/28 |
| 1,430,033 A | * | 9/1922 | Smerschnik | 15/104.09 |
| 1,911,973 A | * | 5/1933 | Ruse | 15/28 |
| 1,927,566 A | * | 9/1933 | Hawk | 15/23 |
| 2,250,975 A | * | 7/1941 | Sussman | 15/22.1 |
| 2,655,674 A | * | 10/1953 | Grover | 15/23 |
| 2,662,239 A | * | 12/1953 | Grover | 15/23 |
| 2,911,660 A | * | 11/1959 | Klemas et al. | 15/28 |
| 3,732,589 A | * | 5/1973 | Burki | 15/22.1 |
| 3,984,890 A | * | 10/1976 | Collis | 15/22.1 |
| 5,071,348 A | * | 12/1991 | Woog | 433/118 |
| 5,500,970 A | * | 3/1996 | Maurer et al. | 15/22.1 |
| 6,253,404 B1 | * | 7/2001 | Boland et al. | 15/22.1 |
| 6,343,396 B1 | * | 2/2002 | Simovitz et al. | 15/27 |
| 6,647,577 B2 | * | 11/2003 | Tam | 15/28 |
| 7,185,383 B2 | * | 3/2007 | Gatzemeyer et al. | 15/28 |
| 2003/0079305 A1 | * | 5/2003 | Takahata et al. | 15/22.1 |

* cited by examiner

*Primary Examiner*—Gary K Graham
(74) *Attorney, Agent, or Firm*—Joseph Pagnotta

(57) ABSTRACT

An electric toothbrush attachment includes a longitudinal body extending in a first direction substantially away from an attachment location for attaching the longitudinal body to an electric toothbrush drive unit and a brush connected to an end of the longitudinal body, the brush having bristles extending in a second direction substantially inopposite to the first direction. The longitudinal body transitions into a proximal end having a brush mount portion via a transition region between the longitudinal body and the proximal end. The transition region is formed as an angle of approximately 90° between the longitudinal body and the proximal end. The proximal end further includes a brush mount portion that is adapted to hold a brush.

3 Claims, 5 Drawing Sheets

ELECTRIC TOOTHBRUSH ATTACHMENT FOR BACKSIDE CLEANING

BACKGROUND OF THE INVENTION

1. Field of the Invention

Embodiments of the invention generally relate to an apparatus for promoting dental hygiene. More specifically, an apparatus is presented for cleaning the backside of teeth in the human mouth.

2. Description of the Related Art

Conventional toothbrushes have been in existence for quite some time and employ a rather typical and simple design. This design facilitates cleaning of the front side of the teeth (i.e., the side that is most visible when smiling or otherwise exposing the teeth). However, the orientation of human hands coupled with convention toothbrush design and ergonomics diminishes the ability to clean the backside of teeth (i.e., the side opposite the front side not normally visible without assistance of a mirror of similar device). This condition promotes incomplete and improper oral hygiene and the long term effects from same including tooth decay, gum disease, frequent and/or expensive periodontal procedures and the like.

Electric toothbrushes offered to solve some of the above presented deficiencies in oral hygiene by their superior cleaning ability. A brush attached to a rotating, oscillating or vibrating drive assembly generates far more revolutions or oscillations per minute than the human hand so as to promote more efficient and complete tooth cleaning. However, the designs of the brush assemblies remain substantially similar to the convention toothbrush design and do not allow for effective or complete cleaning of the backside of teeth. For example, FIG. 1 depicts a prior dental cleaning device 1 in the form of an electric toothbrush as seen in U.S. Pat. No. 5,836,030 issued Nov. 17, 1998 to Hazeu et. al. and FIG. 4 depicts a side view of the right side of the human skull 40 and jaws 42 showing teeth 44 (i.e., the front side or outside of the teeth) arranged therein. The angle, location and arrangement of a brush-head portion 8 of the cleaning device 1 create a condition whereby the cleaning device 1 cannot effectively reach a backside (not visible) of all the teeth. This is most particularly experienced by the central and lateral incisors 46 which are the front-most teeth in the human mouth. Additionally, brushing the backside of the incisors in this manner is awkward or uncomfortable to the cleaning device operator. Therefore, the problem of incomplete care of the backside of teeth still exists despite the technological improvements.

Thus, there is a need in the art for an improved apparatus for cleaning teeth.

SUMMARY OF THE INVENTION

The disadvantages associated with the prior art are overcome by embodiments of an electric toothbrush attachment. In one embodiment the apparatus includes a longitudinal body extending in a first direction substantially away from an attachment location for attaching the longitudinal body to an electric toothbrush drive unit and a brush connected to an end of the longitudinal body, the brush having bristles extending in a second direction substantially inopposite to the first direction. The longitudinal body transitions into a proximal end having a brush mount portion via a transition region between the longitudinal body and the proximal end. The transition region is formed as an angle of approximately 90° between the longitudinal body and the proximal end. The proximal end further includes a brush mount portion that is adapted to hold a brush. In one embodiment, the brush is held to the brush mount portion by one axle that allows a pivoting/pendulum-like movement of the brush. In a second embodiment, the brush is held to the brush mount portion by two or more axles that support a corresponding number of gears that allow a circular movement of the brush.

BRIEF DESCRIPTION OF THE DRAWINGS

The teachings of the present invention will become apparent by considering the following detailed description in conjunction with the accompanying drawings, in which.

Where possible, identical reference numerals are used herein to designate identical elements that are common to the figures. The images in the drawings are simplified for illustrative purposes and are not depicted to scale.

The appended drawings illustrate exemplary embodiments of the invention and, as such, should not be considered as limiting the scope of the invention that may admit to other equally effective embodiments.

DETAILED DESCRIPTION

Figure 1:
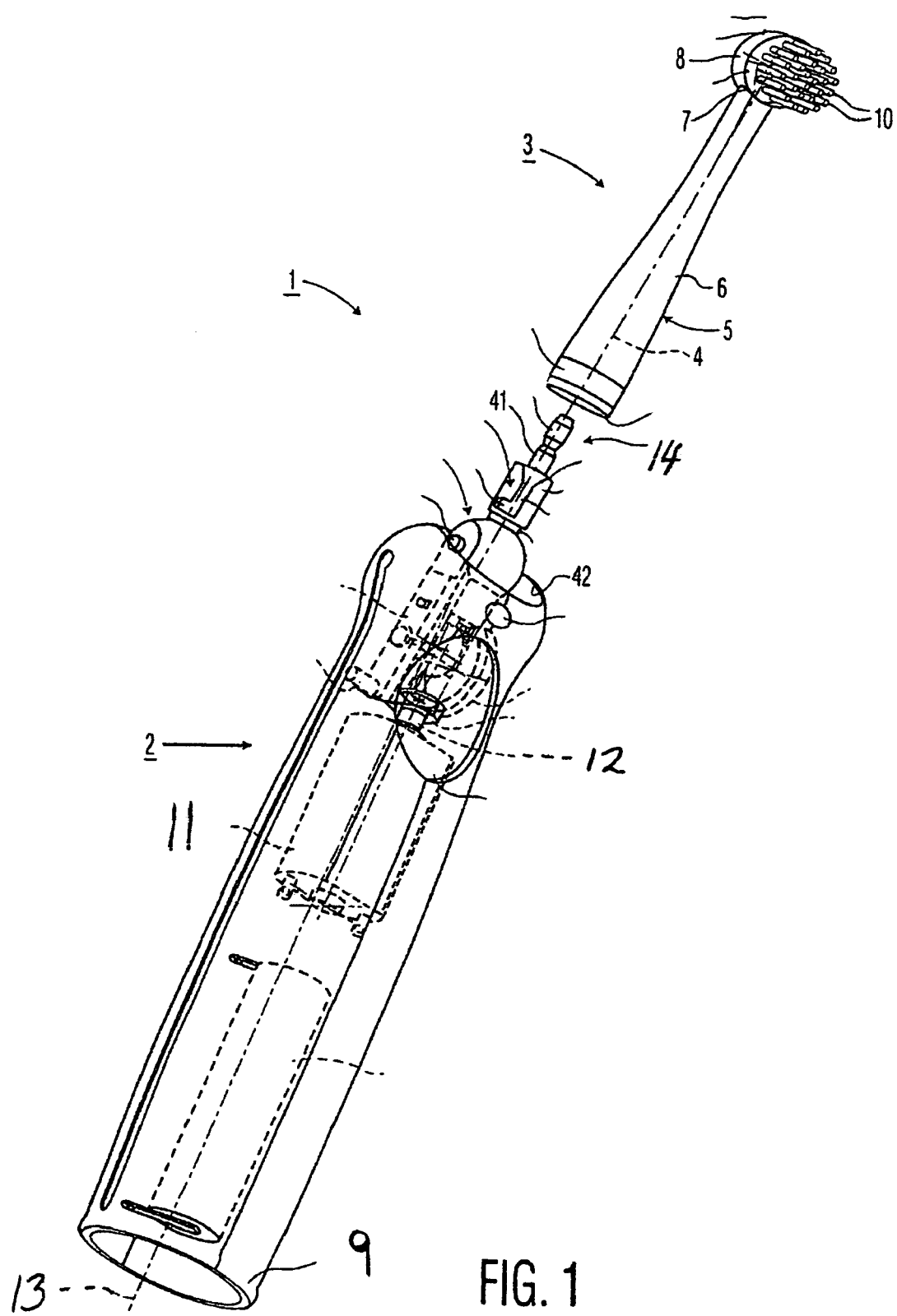
FIG. 1 depicts a prior dental cleaning device in the form of an electric toothbrush.

The subject invention relates to a dental cleaning device attachment that is capable of being attached to a modular-type dental cleaning device to facilitate and improve the cleaning of the backside of teeth. A non-limiting example of such a modular dental cleaning device is seen in the aforementioned U.S. Pat. No. 5,836,030 to Hazeu et. al. and shown in FIG. 1. The device 1 includes a grip member 2 to be held in the hand and an attachment 3. The attachment 3 includes an extension member 5 which extends along a longitudinal axis 4 and projects from the grip member 2 in the direction of the longitudinal axis 4. The extension member includes a tubular portion 6, which tapers down away from the grip member 2, a brush-head portion 8, which is integrally connected to the tubular portion 6 at an end 7 of the tubular portion 6 which is remote from the grip member 2, as well as bristles 10.

The grip member 2 includes a housing 9, which accommodates a motor 11, having a drive shaft 12 which extends parallel to a longitudinal axis 13 of the grip member 2. The motor 11 has a drive means 14, which is situated partly in the grip member 2 and partly in the attachment 3. A coupling shaft 41 makes up part of the drive means 14 and projects in the direction of the longitudinal axis 4 of the attachment 3 and interior of the housing 9 through an opening 42 in the housing 9 of the grip member 2 at the brush-head side. Through a series of mechanical interconnections, the coupling shaft 41 is connected to the motor 11 and the brush-head portion 8 so as to provide rotational and or vibrational movement to the brush-head portion 8. However, the attachment 3 is ill-suited for performing cleaning functions for the backside of teeth and especially incisors.

Figure 2A:
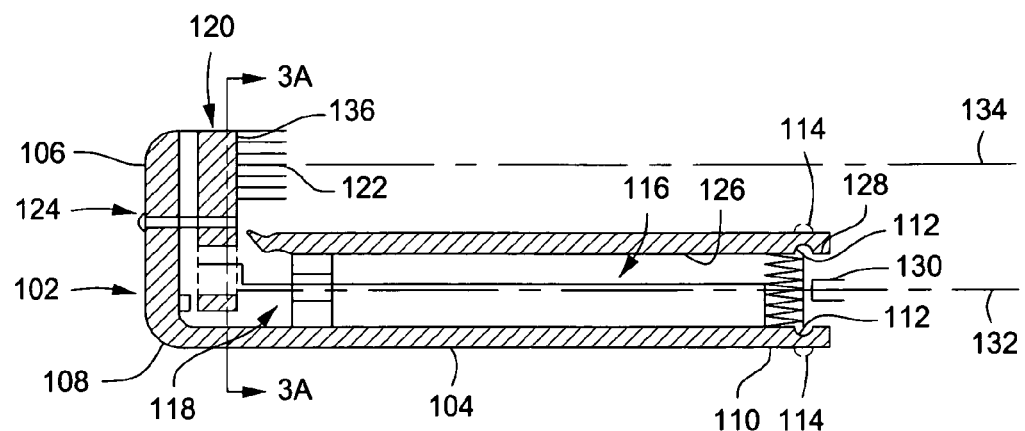
FIG. 2A depicts a partial elevation, partial cross-sectional view of a cleaning device attachment in accordance with a first embodiment of the subject invention.

FIG. 2A depicts a cleaning device attachment 100 in accordance with a first embodiment of the subject invention for performing the discussed backside teeth cleaning. The overall shape, design and configuration of components are shown as a non-limiting example. Slight variations of same are possible without departing from the spirit and scope of the invention. Specifically, the attachment 100 comprises a longitudinal body 104 that defines a first longitudinal axis 132 therein. The longitudinal body 104 extends from a distal end 110 (that is capable of attaching to a drive unit (not shown)) to a proximal end 102. Further, the longitudinal body 104 transitions, via a transition portion 108, to the proximal end 102. The longitudinal body 104 is comprised of a material that is sufficiently rigid and strong to support itself and its mechanical components as well as withstand the forces exerted thereupon when attached to a cleaning device and undergoing a dental cleaning operation. Such material is selected from the group consisting of plastics, metals and alloys. In one embodiment of the invention, the transition portion 108 is approximately 90° such that the longitudinal body 104 and proximal end 102 are at a substantially right angle to one another.

At the proximal end 102 of the longitudinal body 104 is a brush head mount portion 106 which is used to attach a brush 120. Preferably the brush 120 is attached in a manner that permits rotation of the brush 120 about at least one pivot point. In one embodiment of the invention, a single pivot point is defined by an axle 124 secured to the brush head mount portion 106 and received by an opening 206 (see FIG. 3A or 3B) in the brush 120 that rotatably connects the brush 120 to the brush mount portion 106. The axle 124 is selected from the group consisting of a rivet, stud, nut and bolt arrangement, dowel or pin. Other axle configurations are possible without departing from the spirit and scope of the invention. In a second embodiment of the invention depicted in FIG. 2B, at least two pivot points are defined by at least two axles $124_1$ and $124_2$ that are received by at least two openings $206_1$ and $206_2$ (see FIG. 3C) in the brush 120 that rotatably connects the brush 120 to the brush mount portion 106. The axles 124 are selected the group consisting of a rivets, studs, nut and bolt arrangements, dowels or pins that rotatably connect the brush 120 to the brush mount portion 106. Other axle configurations are possible without departing from the spirit and scope of the invention.

The brush 120 comprises a plurality of bristles 122 mounted perpendicularly to a bristle mounting surface of the brush 120. The bristles 122 are comprised of a material that provides sufficient and satisfactory levels of scrubbing/cleaning action and are well known to those skilled in the art to include but not be limited to such materials as nylon and the like. Given that the transition portion 108 is approximately 90°, the longitudinal body 104 and proximal end 102 are at a substantially right angle to one another. Additionally, the bristles 122 of the brush 120 mounted upon the proximal end 102 are at a substantially right angle to the proximal end 102. Accordingly, the bristles 122 extend from the brush 120 in a direction that is substantially inopposite to the direction that the longitudinal body 104 extends. That is, the longitudinal body 104 extends away from a drive unit from the distal end 110 to the proximal end 102. In other words, the bristles 122 extend from the brush 120 in a direction that defines a second longitudinal axis 134 that is substantially parallel to the first longitudinal axis 132. In alternate embodiments of the invention, the bristles 122 may be angled slightly in a plurality of various directions to increase the effectiveness of their cleaning ability. For example, the axle or axles 124 may be gimbal mounted or provided with some means of angling to meet the contours of a tooth surface during a cleaning operation or the bristles 122 can be affixed to the brush 120 at one or more angles. However, since the bristles extend away from the brush 120, it is understood that the net direction of the bristles is substantially perpendicular from the brush 120 thereby defining the second longitudinal axis 134 that is substantially parallel to the first longitudinal axis 132.

At a distal end 110 of the longitudinal body 104, is a connection means 112/114 for connecting the attachment 100 to a drive means of a dental cleaning device. For example, in one embodiment, the connection means 112/114 connects attachment 100 to grip member 2 of the device 1 in FIG. 1. In one embodiment, the connection means is a groove or plurality of recesses 112 provided on a inner surface 126 of the longitudinal body 104. Such groove or plurality of dimples 112 would communicate with a corresponding ring or plurality of bumps on the grip member 2 (not shown). In an alternate embodiment of the invention, the connection means is a ring or plurality of bumps 114 provided on an outer surface 128 of the longitudinal body 104. Such ring or plurality of bumps 114 would communicate with a corresponding groove or plurality of recesses on the grip member 2 (not shown). Other types of attachment may be employed by those skilled in the art while still retaining the scope and spirit of the invention including but not limited to rotatable cam-lock configuration, threaded longitudinal body 104 and grip member 2, clips and the like.

Also at the distal end 110 of the attachment 100 is a coupler 130. The coupler 130 is used to couple mechanical power from a power source from the modular dental cleaning device to the attachment 100. For example, in one embodiment, the coupler 130 couples the coupling shaft 41 of the grip member 2 of FIG. 1 to a longitudinally extending drive member 116 housed within the longitudinal body 104. The longitudinally extending drive member 116 is comprised of a material that is sufficiently strong to transmit the necessary rotational force to drive a brush yet remain flexible in order to absorb drivetrain shocks from either motor start up or brush dragging from pressure applied thereto. Such material is selected from the group consisting of plastics, metals and alloys and in one embodiment is a wire drive. Approximate the proximal end 102, a bushing 118 is disposed in the longitudinal body 104 to support the drive member 116 and assist in the drive member operating in a non-binding manner.

Figure 3A:
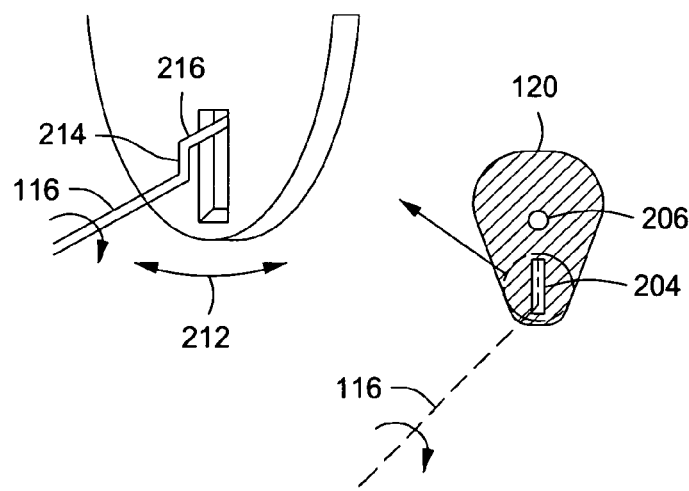
FIG. 3A depicts a cross-sectional view taken along lines 3A-3A of FIG. 2A of a first embodiment of a brush mount in accordance with the subject invention.

The drive member 116 terminates at the proximal end 102 of the longitudinal body 104 and is mechanically coupled to the brush 120. FIGS. 3A, 3B and 3C depict cross-sectional views of the brush 120 taken along lines 3A-3A, 3B-3B and 3C-3C of FIGS. 2A, 2B and 2C to further depict various embodiments of the mechanical couplings. Therefore, the reader is directed to look at the appropriate combination of FIGS. 2 and 3 simultaneously as directed below.

A first embodiment of the brush 120 mechanically coupled to drive member 116 is seen in FIGS. 2A and 3A. Specifically, drive member 116 terminates in a recess 204 in the brush 120. In this first embodiment, the recess 204 is formed as a narrow slot. The drive member 116 (starting as a substantially straight component) is provided with an angled transition section 214 followed by a terminating section 216 that is received in the narrow slot (recess) 204. In one embodiment, an angled transition section 214 and terminating section 216 are formed at right angles to one another and the drive member 116 so as to resemble an "S" shape. Upon rotation of the drive member 116 (denoted by arrow), the brush 120 oscillates in a pendulum-like manner 212 about pivot point 124/206. Such pendulum-like oscillations allow the bristles 122 to vibrate at a rate and in a manner so as to facilitate cleaning of teeth.

Figure 2B:
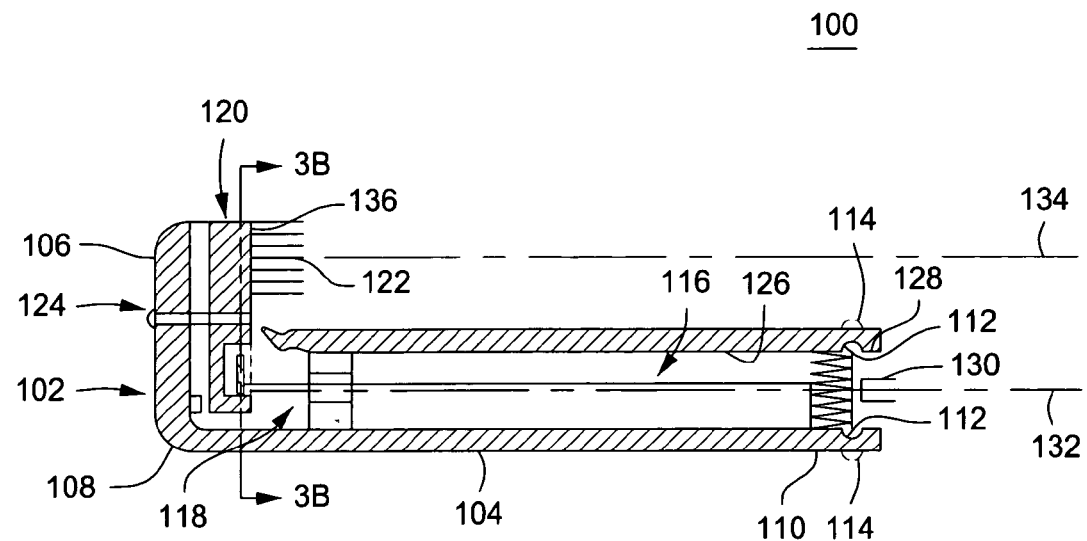
FIG. 2B depicts a partial elevation, partial cross-sectional view of a cleaning device attachment in accordance with a second embodiment of the subject invention.
Figure 3B:
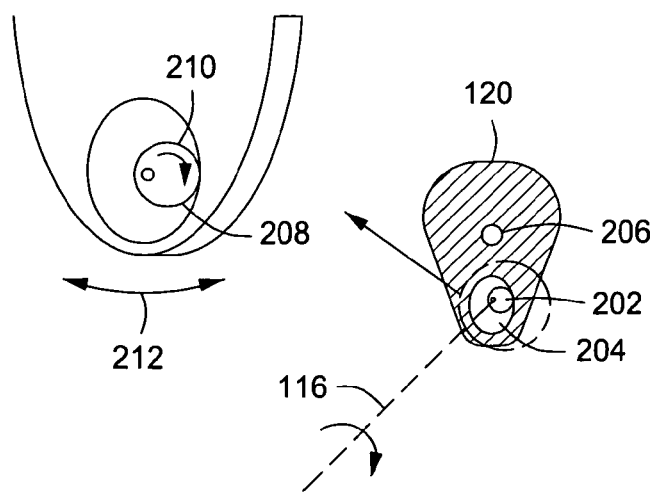
FIG. 3B depicts a cross-sectional view taken along lines 3B-3B of FIG. 2B of a second embodiment of a brush mount in accordance with the subject invention.
Figure 3C:
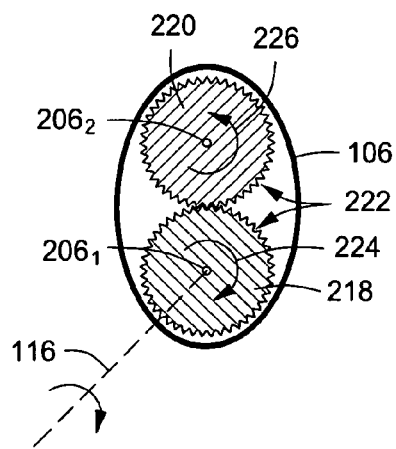
FIG. 3C depicts a cross-sectional view taken along lines 3C-3C of FIG. 2C of a third embodiment of a brush mount in accordance with the subject invention.

A second embodiment of the brush 120 mechanically coupled to drive member 116 is seen in FIGS. 2B and 3B. Specifically, drive member 116 terminates in a recess 204 in the brush 120. In this second embodiment, the recess 204 is formed substantially as an oval. The drive member 116 is provided with a cam lobe 202 which is received in the recess 204. Upon rotation of the drive member 116 (denoted by arrow), the cam lobe 202 eccentrically rotates such that its outer surface 208 contacts an inner surface 210 of the recess 204. As such, the brush 120 oscillates in a pendulum-like manner 212 about pivot point 124/206. Such pendulum-like oscillations allow the bristles 122 to vibrate at a rate and in a manner so as to facilitate cleaning of teeth.

Figure 2C:
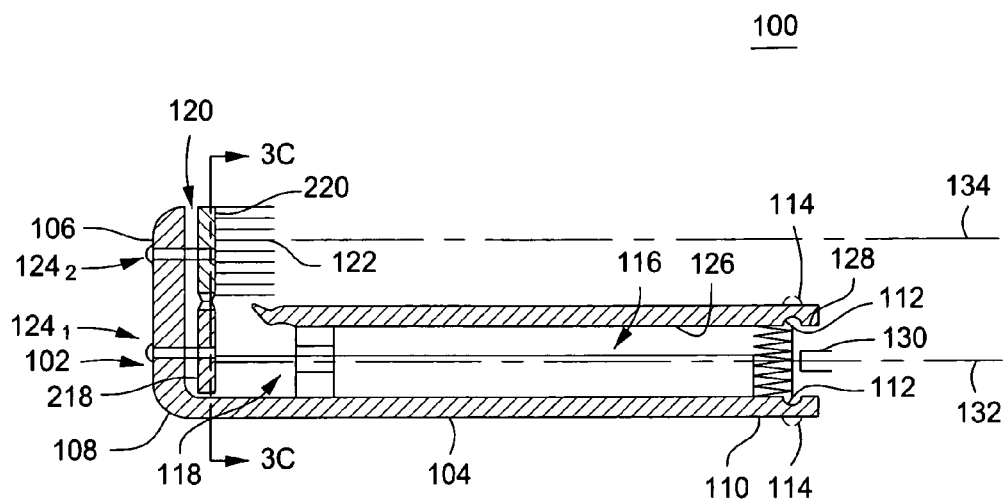
FIG. 2C depicts a partial elevation, partial cross-sectional view of a cleaning device attachment in accordance with a third embodiment of the subject invention.

A third embodiment of the brush 120 mechanically coupled to drive member 116 is seen in FIGS. 2C and 3C. Specifically, drive member 116 terminates at and is connected to a first brush gear 218. First brush gear 218 meshes with second brush gear 220 via gear teeth 222. Upon rotation of the drive member 116 (denoted by arrow), the first brush gear 218 rotates in the same direction of rotation 224 about a first pivot point $124_1/206_1$. Such rotation causes the second brush gear 220 to rotate in an opposite direction of rotation 226 about a second pivot point $124_2/206_2$. The second brush gear 220 has the plurality of bristles 122 affixed thereto which subsequently rotate at a rate and in a manner so as to facilitate cleaning of teeth. Alternately, second brush gear 220 is provided with a disc, eccentric mount or the like to facilitate an orbital or vibratory motion rather than just a purely rotational motion for cleaning of teeth. The first brush gear 218 can be smaller in diameter than the second brush gear 220 for increased power and to make the longitudinal body 104 easier to fit into the operator's mouth. In one embodiment of the invention, the ratio of the first brush gear 218 to the second brush gear 220 is 2:1. Although a ratio of 1:1 is depicted in the Figures, any ratio that allows for proper operation of the device and cleaning of the teeth can be substituted for the shown ratios and remain within the spirit and scope of the invention.

Figure 4:
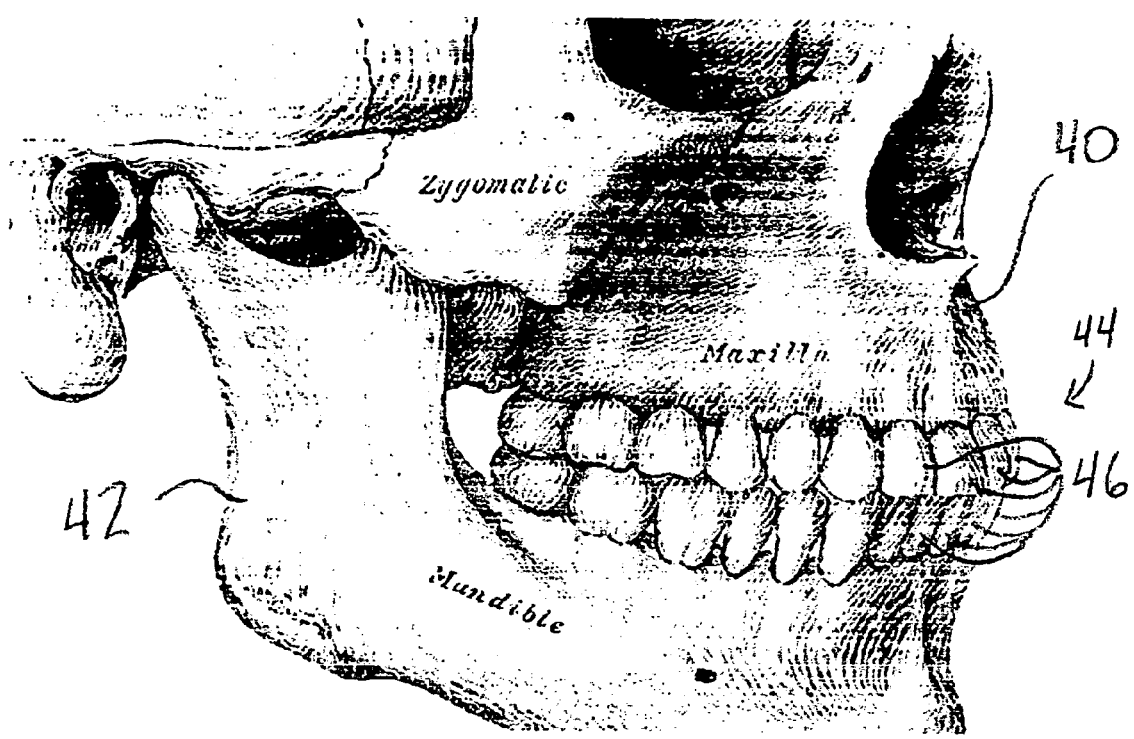
FIG. 4 depicts a side view of the right side of the human skull and jaws showing teeth (i.e., the front side or outside of the teeth) arranged therein.

Inspection of at least FIGS. 2A-2C in comparison to FIG. 4 reveals the advantages of the above-described attachment. Specifically, the bristles 122 are turned so that they are facing in an opposite direction to that of the longitudinal body 104. In other words, they are extending in a direction that is parallel to the axis 132 of the longitudinal body 104. With the arrangement so described, the backsides of teeth (and particularly incisors 46) can be easily cleaned by using movements similar to those that would be used with other attachments that are used for cleaning molars. That is, a gentle back and forth, slightly angled or up and down movement is possible without having to severely angle the cleaning device so that it is nearly perpendicular with an operator's face. Such severely angled position is uncomfortable because of the proximity of the cleaning device to the face, eyes, chin, etc which would otherwise cause the operator to shorten cleaning time associated with these teeth or suffer hand or jaw cramping needlessly. The aforementioned attachment reduces the discomfort associated with this part of the dental hygiene regimen.

While the foregoing is directed to embodiments of the present invention, other and further embodiments of the invention may be devised without departing from the basic scope thereof, and the scope thereof is determined by the claims that follow.

What is claimed is:

1. An electric toothbrush attachment comprising:
a longitudinal body extending in a first direction substantially away from an attachment location for attaching the longitudinal body to an electric toothbrush drive unit, the longitudinal body transitioning into a proximal end via a transition region between the longitudinal body and the proximal end, the proximal end having a brush mount portion holding a brush by two or more axles that support a corresponding number of gears that allow a circular movement of the brush, the brush having bristles extending in a second direction substantially inopposite to the first direction and capable of having a pivoting motion about an axis parallel to the first direction.

2. An electric toothbrush attachment comprising:
an elongated attachment body that transitions into a proximal end having a brush mount portion via a transition region between the attachment body and the proximal end;
a brush mounted perpendicularly to the attachment body with respect to a longitudinal axis of the attachment body, the brush mount portion holding the brush by two or more axles that support a corresponding number of gears that allow a circular movement of the brush; and
a plurality of bristles extending perpendicularly away from a bristle mounting face of the brush and having a pivoting motion about an axis parallel to the longitudinal axis.

3. An electric toothbrush attachment comprising:
an elongated attachment body that transitions into a proximal end having a brush mount portion via a transition region between the attachment body and the proximal end, the attachment body having a longitudinally extending drive member; the brush mount portion is holding a brush by two or more axles that support a corresponding number of gears that allow a circular movement of the brush, the brush communicating with said longitudinally extending drive member and having bristles extending substantially parallel with said longitudinally extending drive member and having a pivoting motion about an axis parallel to the longitudinally extending drive member.

* * * * *